(12) United States Patent
Roajanasiri et al.

(10) Patent No.: US 8,256,272 B1
(45) Date of Patent: Sep. 4, 2012

(54) UV ADHESIVE VISCOSITY ADJUSTMENT APPARATUS AND METHOD

(75) Inventors: Reangroaj Roajanasiri, Thanyaburi (TH); Buatip Buasak, Thanyaburi (TH)

(73) Assignee: Western Digital (Fremont), LLC, Fremont, CA (US)

( * ) Notice: Subject to any disclaimer, the term of this patent is extended or adjusted under 35 U.S.C. 154(b) by 343 days.

(21) Appl. No.: 12/646,926

(22) Filed: Dec. 23, 2009

(51) Int. Cl.
*G01N 11/14* (2006.01)

(52) U.S. Cl. ..................................................... 73/54.31

(58) Field of Classification Search ............... 73/54.23, 73/54.28–54.33, 54.35; 366/152.3, 152.5
See application file for complete search history.

(56) References Cited

U.S. PATENT DOCUMENTS

| | | | | |
|---|---|---|---|---|
| 3,965,722 A | * | 6/1976 | Bagg et al. ............... | 73/54.31 |
| 4,539,838 A | * | 9/1985 | Fraleigh .................. | 73/54.23 |
| 4,546,438 A | * | 10/1985 | Prewitt et al. ............ | 700/198 |
| 4,559,812 A | * | 12/1985 | Kitchen .................. | 73/54.32 |
| 5,590,560 A | * | 1/1997 | Joos et al. ............... | 73/64.48 |
| 6,711,941 B2 | * | 3/2004 | Braithwaite et al. ...... | 73/54.01 |
| 6,854,349 B2 | * | 2/2005 | Brandhorst et al. ....... | 73/866 |
| 7,331,703 B1 | * | 2/2008 | Hahn et al. .............. | 366/152.5 |
| 2002/0116987 A1 | * | 8/2002 | Braithwaite et al. ...... | 73/54.01 |
| 2011/0203384 A1 | * | 8/2011 | Wilkinson et al. ........ | 73/788 |
| 2011/0252871 A1 | * | 10/2011 | Nagoshi et al. .......... | 73/54.02 |

FOREIGN PATENT DOCUMENTS

JP   2005098951 A   *  4/2005

* cited by examiner

*Primary Examiner* — John Fitzgerald

(57) ABSTRACT

Examples of an apparatus and method for adjusting a viscosity of an adhesive are disclosed. An apparatus may comprise a motor including a spindle. A tooling bit may be disposed spaced from and axially aligned with the spindle extending into a first end of a syringe to contact an adhesive in the syringe while the syringe is detachably mounted for rotation to the spindle. A lamp may selectively shine a curing light on the adhesive. A meter may be coupled to the motor to measure a torque on the motor. The method may include detachably mounting the syringe containing the adhesive to the motor. The motor may be operated to stir the adhesive at a first voltage for a predetermined time. A torque on the motor may be measured and compared to a reference range of values.

15 Claims, 3 Drawing Sheets

UV ADHESIVE VISCOSITY ADJUSTMENT APPARATUS AND METHOD

BACKGROUND

The subject disclosure relates to adhesives, and more particularly, to UV adhesive viscosity adjustment apparatuses and methods thereof.

Certain adhesives may be preferred in the controlled coupling of relatively small mechanical components. One exemplary application includes the coupling of hard drive assembly components where the spread of adhesive may be significant in controlling the contamination of adjacent components during adhesion and subsequent curing. The spread of adhesive may be related to its viscosity.

Significant amounts of adhesive may be employed during the construction of hard drive components in large scale manufacturing environments. Variations in viscosity can be due to manufacturing inconsistencies as well as environmental changes as the adhesive is shipped from the supplier to the client. Adhesives may be obtained in relatively large lot size quantities and thus, the rejection and return of an entire lot due to the adhesive being out of specification may be counterproductive to cost-effectiveness in a manufacturing environment.

Accordingly, there is a need for an apparatus and method of adjusting viscosity in an adhesive at the application level.

SUMMARY

In one aspect of the disclosure, a viscosity adjustment apparatus includes a motor including a spindle projecting distally from the motor. The apparatus also includes a tooling bit disposed spaced from and axially aligned with the spindle. The tooling bit is configured to extend into a first end of a syringe and contact an adhesive present in the syringe while a second end of the syringe is detachably mounted for rotation to the spindle. A lamp is configured to selectively shine a curing light on the adhesive. A meter is coupled to the motor configured to measure a torque on the motor generated by stirring the adhesive with the elongated bit during operation of the motor.

In another aspect of the disclosure, a method of adjusting a viscosity in an adhesive, includes detachably mounting a syringe containing an adhesive to a motor, wherein an elongated bit extends into the syringe in contact with the adhesive. The method also includes operating the motor at a first voltage for a predetermined time. A torque on the motor generated by stirring the adhesive with the elongated bit during operation of the motor is measured. The measured torque is compared to a reference range of values.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
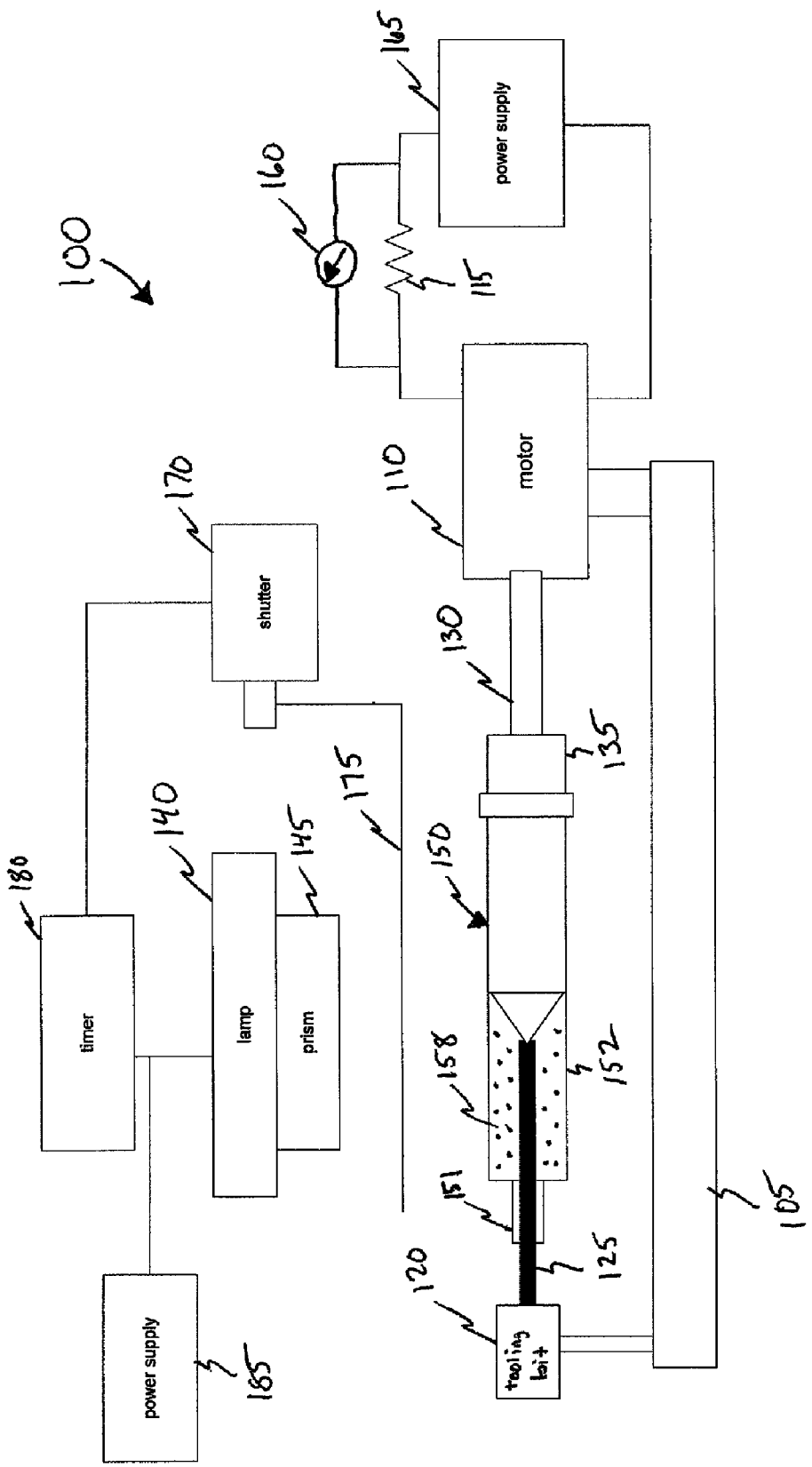
FIG. 1 is a block diagram illustrating an example of a viscosity adjustment apparatus.

FIG. 1 shows a viscosity adjustment apparatus 100 according to one aspect of the subject technology. The viscosity adjustment apparatus 100 includes a motor 110, a tooling bit 120, a lamp 140, and a meter 160. The motor 110 includes a spindle 130 projecting distally from the motor 110. The spindle 130 is rotated by operation of the motor 110. The tooling bit 120 includes a shaft 125 extending axially from the tooling bit 120.

In one aspect, the viscosity adjustment apparatus 100 is configured to detain a syringe 150 containing an adhesive 158 and measure the viscosity of the adhesive 158. The motor 110 and tooling bit 120 may be mounted onto a mount 105. The tooling bit 120 may be disposed spaced from and in axial alignment with the spindle 130. The shaft 125 may be disposed to extend into an open ended nozzle 151 of the syringe 150 and make contact with the adhesive 158 contained in the tube 152. A second end of the syringe 150 is detachably mounted to a chuck 135 attached to the spindle 130.

The motor 110 may be coupled to a power supply 165 delivering between 0-30 volts to the motor 110. A resistor 115 may be coupled between the motor 110 and the power supply 165. The resistor 115 may be an adjustable-type resistor. The resistor 115 may have a resistance value of 1 ohms to 5 ohms. A higher resistance value, for example, 5 ohms as compared to 1 ohm, may be employed when a higher sensitivity to current variation flowing to the motor 110 may be desired. In one exemplary configuration, the resistor 115 may be fixed at 5 ohms while 1 volt is delivered to the motor 110 by the power supply 165. The meter 160 may be coupled to the resistor 115 to measure a voltage across the resistor as a torque is generated on the motor 110 during rotation of the syringe 150 containing the adhesive 158.

During operation of the motor 110, the spindle 130 spins the syringe 150 around the shaft 125. The adhesive 158, which is inside the syringe 150, is also spun about the shaft 125. The shaft 125, which is in contact with the adhesive 158, stirs the adhesive 158 during spinning. In one aspect, the adhesive 158 may be viscous enough to adhere to the shaft 125 during spinning. As the adhesive 158 is stirred, agitation of the adhesive 158 may change the viscosity of the adhesive 158. As the adhesive 158 is agitated by contact with the shaft 125, the adhesive 158 imparts a torque back upon the spindle 130 and the motor 110. A change in the torque imparted back onto the motor 110 may signify a change in the viscosity of the adhesive 158.

The amount of torque imparted back upon the motor 110 may be indirectly measured by the meter 160. In one aspect, the torque may be determined by measuring the voltage across the resistor 115. The power supply 165 may supply a fixed voltage to the motor 110 and the resistance of the resistor 115 may be fixed. As the adhesive 158 changes in viscosity, the torque imparted back onto the motor 110 will vary and the current flowing to the motor 110 will vary based on the changing torque. As the current varies, the voltage across the resistor 115 will vary indicating increasing or decreasing torque on the motor 110. For example, the current flowing to the motor 110 operating with a 1 volt supply may measure 0.35 amps without a syringe 150 containing the adhesive 158 mounted to the motor 110. When the syringe 150 and the adhesive 158 are mounted to the motor 110 and the adhesive is agitated, the current may drop to 0.27 amps and the voltage measured across the resistor 115 with a resistance of 2.85 ohms may be 0.77 volts. Thus, levels of voltage across the resistor 115 may be associated with certain levels of viscosity for a given adhesive spun at a fixed voltage supplied to the motor 110.

Accordingly, a range of reference voltage values may be established by mounting a sample of an adhesive that has a viscosity within an acceptable range of viscosity values to the viscosity adjustment apparatus 100 and measuring the voltage across the resistor 115. The motor 110 may be operated at a reference operating voltage level to establish the range of reference measured voltage values for comparison to subsequent samples of a given adhesive. For example, the motor 110 may be supplied with a reference operating voltage of 1 volt to turn the spindle 130 and rotate the syringe 150 around the tooling bit 120. The voltage level across the resistor 115 may then be recorded as associated with an acceptable viscosity value for that type of adhesive.

Subsequent samples of adhesive that are determined to be outside an acceptable range of viscosity may be mounted to the viscosity adjustment apparatus 100 and agitated to adjust their respective viscosity. For example, an adhesive with a viscosity determined to be outside the range of acceptable viscosities may be mounted and agitated until the viscosity lowers. The amount of time the adhesive is agitated may be based on, for example, a difference in viscosity between the current viscosity of the adhesive and the acceptable range of viscosity values. The current viscosity may be associated with a currently measured voltage value. The acceptable range of viscosity values may be associated with the range of reference voltage values measured for adhesives 158 with acceptable viscosities. Thus, for a given viscosity, the amount of time the adhesive is agitated may be predetermined by mathematical calculation or by trial and error to bring the currently measured voltage value within the range of reference voltage values. A typical duration for agitating an adhesive 158 is approximately four minutes.

The lamp 140 is disposed to selectively shine a curing light on the adhesive 158 present in the syringe 150. In one aspect, the lamp 140 may be ultraviolet (UV) light. The lamp 140 may also include a prism 145 coupled to the lamp 140 to focus the curing light onto the syringe 150 and the adhesive 158. In one aspect, the prism 145 may filter the light from the lamp 140 to filter out non-UV light. In one aspect, the prism 145 may filter out light from the lamp 140 to allow UV light within a range of UV wavelengths through the prism. The UV wavelengths allowed through the prism 145 may be within a range rated for activating curing in the adhesive 158. A timer 180 may be coupled to the lamp 140 and to a shutter module 170 that is configured to move a shutter 175. The shutter 175 may be positioned between the lamp 140 and the syringe 150 and intermittently displaced to control exposure of curing light from the lamp 140 onto the syringe 150 and the adhesive 158. A power supply 185 may be coupled to the lamp 140, the timer 180, and to the shutter module 170 providing power to each component as needed.

In one aspect, the timer 180 may control the lamp 140 to shine a curing light on the syringe 150 at predetermined intervals to cure the adhesive 158. For example, the adhesive 158 may need curing when its viscosity is below a predetermined range of viscosity values and additional curing may help increase the viscosity. The lamp 140 may shine with a light intensity greater than 2 watts per centimeter$^2$. The syringe 150 may be static while exposed to the lamp 140 or may be rotated by the motor 110 during exposure to provide a homogeneous curing of the adhesive 158.

In one aspect, the timer 180 may control the shutter module 170 to allow controlled exposure of the curing light from the lamp 140 onto the syringe 150 and adhesive 158. For example, the shutter 175 may be displaceably moved by the shutter module 170 to intermittently expose the syringe 150 to the lamp 140. The timer 180 may control the shutter 175 to expose the lamp 140 at 0.4 second intervals. The timer 180 may also block the exposure of the adhesive 158 to the curing light at 0.4 second intervals. The amount of exposure an adhesive 158 receives may be predetermined based on, for example, a difference in viscosity between the current viscosity of the adhesive and the acceptable range of viscosity values. After exposure to the lamp 140, the adhesive 158 may be spun on the viscosity adjustment apparatus 100 and agitated at the reference operating voltage level where the voltage associated with the changed viscosity of the adhesive 158 is measured across the resistor 115. The process of curing and measuring may be repeated until the viscosity of adhesive 158 is adjusted higher to fall within the range of acceptable viscosity values.

Figure 2:
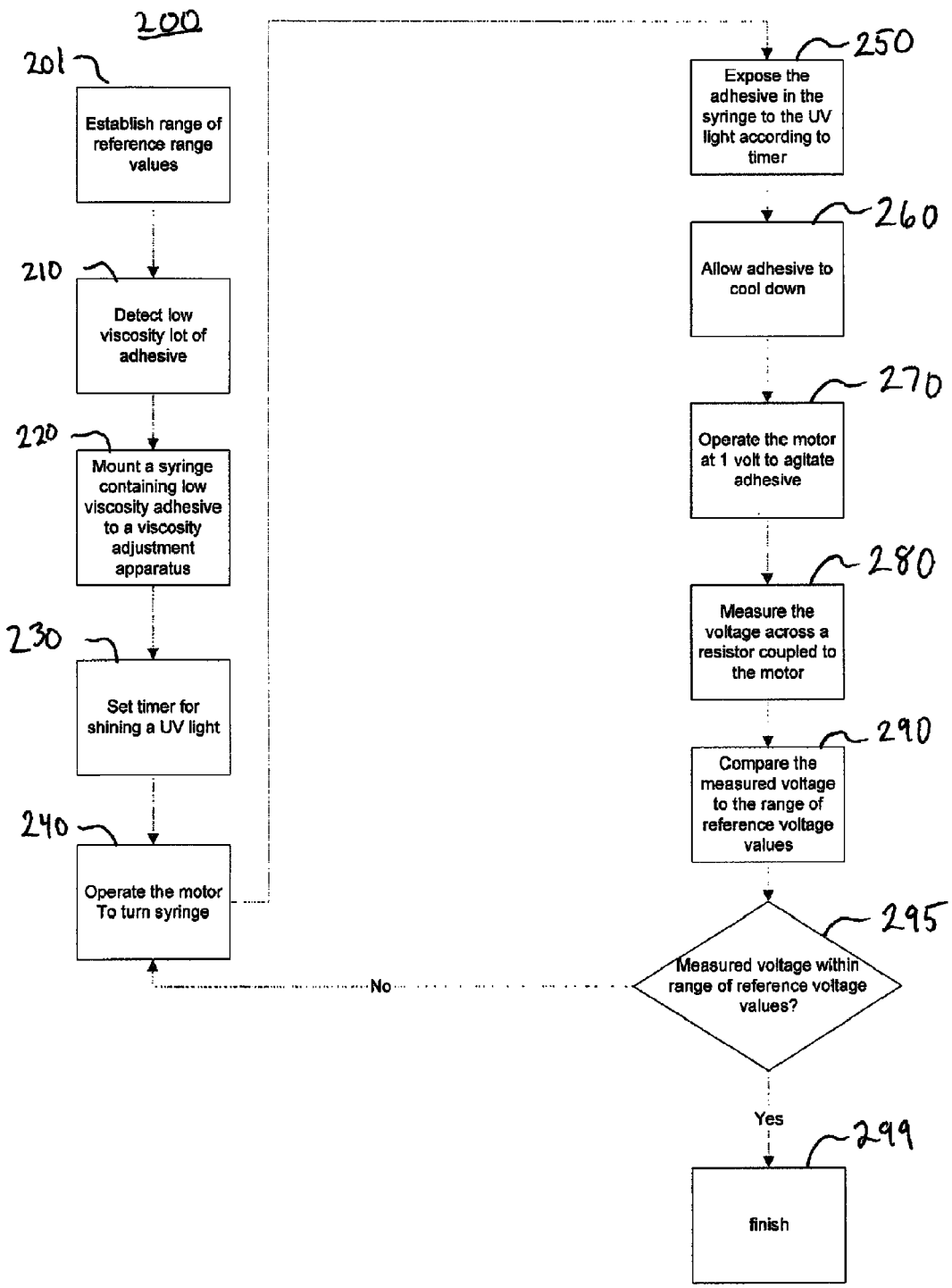
FIG. 2 is a flow chart illustrating an example of a method of adjusting a low viscosity UV adhesive according to certain aspects of the present disclosure.

Referring now to FIG. 2, an exemplary method 200 of adjusting viscosity is shown. In operation 201, a range of measured reference voltage values generated at a reference operating voltage may be established based on an acceptable range of viscosity values for an adhesive. For example, the measured reference voltage values may be based on a torque generated on a motor of a viscosity adjustment apparatus operated at 1 volt. The viscosity adjustment apparatus may be the viscosity adjustment apparatus 100 shown in FIG. 1. The torque may be generated by agitating an adhesive with the motor where the adhesive has a viscosity within a range of acceptable viscosity values. A voltage level across a resistor coupled between the motor and a power supply coupled to the motor during agitation of the adhesive may then be recorded as associated with an acceptable viscosity value for that type of adhesive.

In operation 210, a sample from a lot of adhesive may be checked for viscosity. In one example, the sample may be determined to have a viscosity lower than the acceptable range of viscosity values. For example, an adhesive determined to have a viscosity of approximately 370,000 centipoises (cPs), can be adjusted to a higher viscosity of approximately 420,000 cPs ±2% to 5% by the method 200.

In operation 220, a syringe containing the adhesive determined to be too low in viscosity is mounted to the viscosity adjustment apparatus.

In operation 230, a timer may be set for shining a curing light on the adhesive in the syringe. The duration of exposure an adhesive receives may be based on, a difference in viscosity between the current viscosity of the adhesive and the acceptable range of viscosity values. The lower and farther away from the acceptable range of viscosity values the current viscosity of the adhesive is, the longer the exposure time set by the timer.

In operation 240, the syringe may be rotated by the motor operating at the operating reference voltage level, agitating the adhesive inside the syringe with a tooling bit extending into the syringe stirring the adhesive.

In operation 250, the adhesive may be exposed to the curing light, for example, a UV light, during agitation in intermittent intervals of 0.4 seconds.

In operation 260, the adhesive may be removed from exposure to the curing light and allowed to cool down.

In operation 270, the motor may be operated at the operating reference voltage level to rotate the syringe, agitating the cured adhesive in the syringe so that it generates a torque back onto the motor.

In operation 280, the torque on the motor generated by the cured adhesive being agitated may be measured as a current voltage across the resistor that is coupled between the motor and the power supply supplying the operating voltage to the motor. In operation 290, the currently measured voltage across the resistor is compared to the range of reference voltage values.

In operation 295, a determination is made determining if the currently measured voltage is within the range of reference voltage values. If the currently measured voltage is within the range of reference voltage values, then the method may terminate in operation 299. If the currently measured voltage is not within the range of reference voltage values, then the method may return to operation 240 where the adhesive may be rotated and re-agitated and operation numbers 240 through 295 may be repeated until the currently measured voltage is within the range of reference voltage values associated with an acceptable viscosity.

Figure 3:
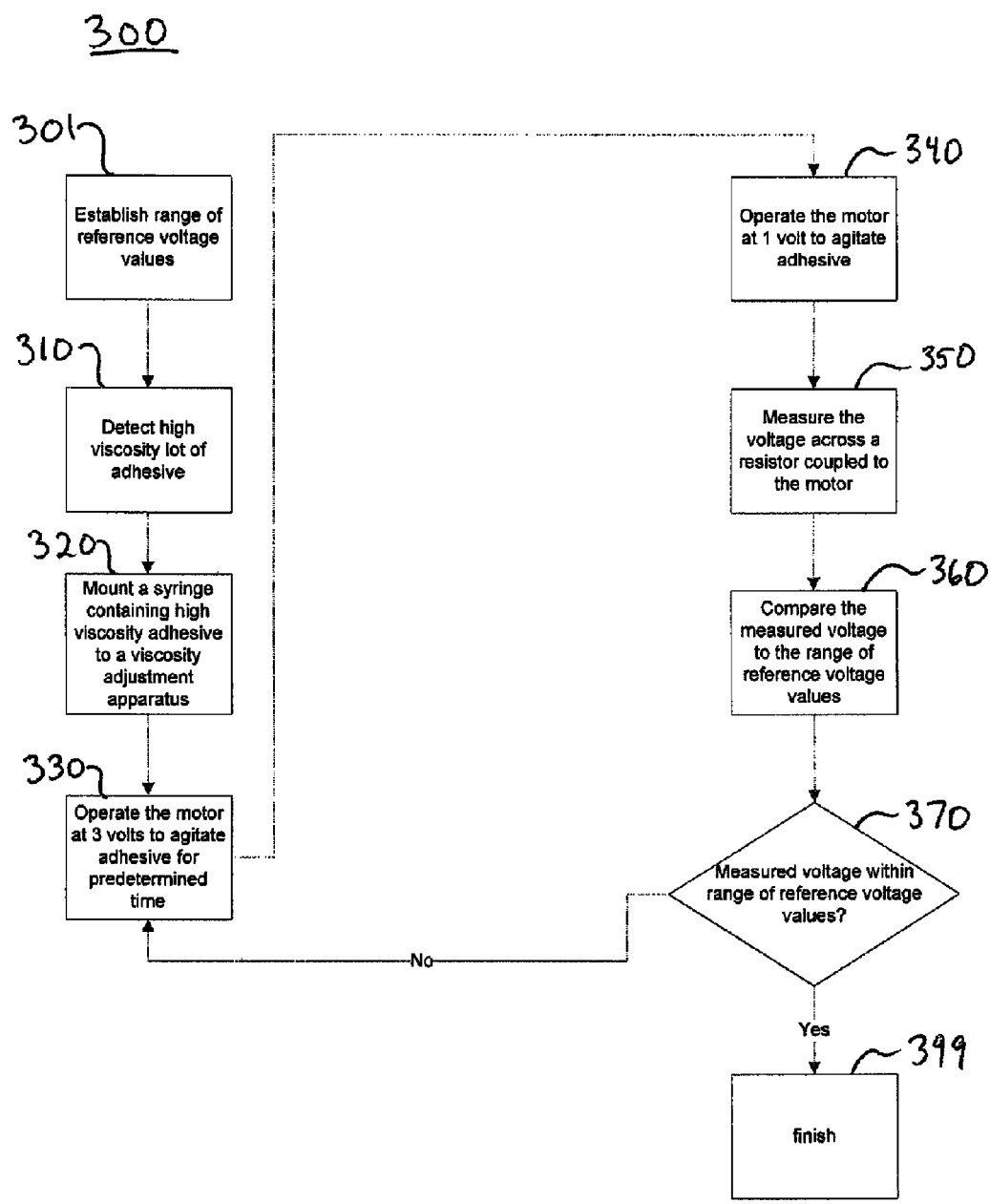
FIG. 3 is a flow chart illustrating an example of a method of adjusting a high viscosity UV adhesive according to certain aspects of the present disclosure.

Referring now to FIG. 3, an exemplary method 300 of adjusting viscosity is shown. In operation 301, a range of measured reference voltage values generated at a reference operating voltage may be established based on an acceptable range of viscosity values for an adhesive. For example, the measured reference voltage values may be based on a torque generated on a motor of a viscosity adjustment apparatus operated at 1 volt. The viscosity adjustment apparatus may be the viscosity adjustment apparatus 100 shown in FIG. 1. The torque may be generated by agitating an adhesive with the motor where the adhesive has a viscosity within a range of acceptable viscosity values. A voltage level across a resistor coupled between the motor and a power supply coupled to the motor during agitation of the adhesive may then be recorded as associated with an acceptable viscosity value for that type of adhesive.

In operation 310, a sample from a lot of adhesive may be checked for viscosity. In one example, the sample may be determined to have a viscosity higher than an acceptable range of viscosity. For example, an adhesive determined to have a viscosity of approximately 600,000 cPs can be adjusted to a lower viscosity of approximately 420,000 cPs ±2% to 5% by the method 300.

In operation 320, a syringe containing the adhesive determined to be too high in viscosity is mounted to the viscosity adjustment apparatus.

In operation 330, the motor attached to the viscosity adjustment apparatus may be operated at a voltage higher than the reference operating voltage. Operating the motor at a higher voltage may increase the rate that the viscosity changes in the adhesive as it is agitated. For example, if the reference operating voltage is 1 volt, then the motor may be operated at 3 volts for a predetermined time to rotate the syringe around a tooling bit in contact with the adhesive to agitate the adhesive and decrease the viscosity of the adhesive in the syringe. The duration of agitation at the higher operating voltage for an adhesive may be based on, a difference in viscosity between the current viscosity of the adhesive and the acceptable range of viscosity values. The higher and farther away from the acceptable range of viscosity values the current viscosity of the adhesive is, the longer the duration of agitation at the higher operating voltage.

In operation, 340, the motor may be operated at the reference operating voltage, for example, 1 volt, to re-establish the reference conditions for torque measurement.

In operation 350, the torque on the motor generated by the adhesive being agitated may be measured as the current voltage across the resistor that is coupled between the motor and the power supply supplying the operating voltage to the motor.

In operation 360, the currently measured voltage is compared to the range of reference voltage values.

In operation 370, a determination is made if the currently measured voltage is within the range of reference voltage values. If the currently measured voltage is within the range of reference voltage values, then the method may terminate in operation 399. If the currently measured voltage is not within the range of reference voltage values, then the method may return to operation 330 where the adhesive may be re-agitated by the motor at the higher operating voltage level for a predetermined amount of time based on, a difference in viscosity between the current viscosity of the adhesive and the acceptable range of viscosity values. Operation numbers 340 through 370 may be repeated until the currently measured voltage across the resistor is within the range of reference voltage values associated with an acceptable viscosity.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A viscosity adjustment apparatus, comprising:
    a motor including a spindle projecting distally from the motor;
    a tooling bit disposed spaced from and axially aligned with the spindle, the tooling bit configured to extend into a first end of a syringe and contact an adhesive present in the syringe while a second end of the syringe is detachably mounted for rotation to the spindle;
    a lamp configured to selectively shine a curing light on the adhesive; and
    a meter coupled to the motor, the meter configured to measure a torque on the motor generated by stirring the adhesive with the elongated bit during operation of the motor.

2. The viscosity adjustment apparatus of claim 1, wherein the curing light is ultraviolet light.

3. The viscosity adjustment apparatus of claim 1, wherein the lamp is controllable to shine the curing light at predetermined intervals.

4. The viscosity adjustment apparatus of claim 1, further comprising a resistor coupled between the motor and a power supply driving the motor, wherein the meter is configured to measure the torque based on a voltage across the resistor.

5. The viscosity adjustment apparatus of claim 1, further comprising a moveable shutter displaceably disposed between the lamp and the syringe.

6. The viscosity adjustment apparatus of claim 5, wherein the shutter is controllable to expose the syringe to the lamp at predetermined intervals.

7. A method of adjusting a viscosity in an adhesive, comprising:
    detachably mounting a syringe containing an adhesive to a motor, wherein an elongated bit extends into the syringe in contact with the adhesive;
    operating the motor at a first voltage for a predetermined time to adjust the viscosity of the adhesive by stirring the adhesive with the elongated bit during operation of the motor;
    measuring a torque on the motor generated by stirring the adhesive with the elongated bit during operation of the motor; and
    comparing the measured torque to a reference range of values.

8. The method of claim 7, further comprising repeating the operating, measuring and comparing steps if the measured torque is not within the range of reference values.

9. The method of claim 7, wherein measuring the torque on the motor comprises:
    operating the motor at a second voltage; and
    measuring a voltage across a resistor coupled between the motor and a power supply driving the motor.

10. The method of claim 9, wherein the second voltage is greater than the first voltage.

11. The method of claim 7, further comprising exposing the adhesive in the syringe to a curing light.

12. The method of claim 11, further comprising allowing the adhesive in the syringe to cool prior to measuring the torque.

13. The method of claim 11, wherein the curing light is ultraviolet light.

14. The method of claim 11, wherein the adhesive in the syringe is exposed to the curing light intermittently during the predetermined time.

15. The method of claim 14, wherein the adhesive in the syringe is exposed to the curing light at intervals of approximately 0.4 seconds.

* * * * *